US006395756B2

(12) United States Patent
Trimming et al.

(10) Patent No.: US 6,395,756 B2
(45) Date of Patent: May 28, 2002

(54) USE OF OPHTHALMIC AGENT

(75) Inventors: Julian Trimming, Forch; Andrea Fetz, Wetzikon, both of (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/741,245

(22) Filed: Dec. 20, 2000

(30) Foreign Application Priority Data

Dec. 23, 1999 (EP) .............................. 99125739

(51) Int. Cl.$^7$ ............................ A61K 31/445
(52) U.S. Cl. ...................... 514/324; 514/912
(58) Field of Search ................. 514/324, 912

(56) References Cited

U.S. PATENT DOCUMENTS 6,207,684 B1 * 3/2001 Aberg ..................... 514/324

FOREIGN PATENT DOCUMENTS

WO      WO99/51230      10/1999

OTHER PUBLICATIONS

Ueda, S., Production of Eye Drop Containing Ketotifen Fumarate, Published Feb. 12, 1987, Patent Abstracts of Japan, Publication No. 62277323.

Toay, N., Published Dec. 12, 1995, Derwent WPI Abstract, Publication No. JP 7324034A.

Christensen, M. et al., Five–Minute Removal of Soft Lenses Prevents Most Absorption of a Topical Ophthalmic Solution, the CLAO Journal, Oct. 1998, pp. 227–231.

European Search Report for EP Patent Application 99125739.5, dated Jun. 14, 2000.

* cited by examiner

*Primary Examiner*—Zohreh Fay
(74) *Attorney, Agent, or Firm*—David E. Wildman

(57) ABSTRACT

The present invention is related to the use an ophthalmic composition comprising ketotifen in the preparation of an eye medicament for the treatment allergic conjunctivitis of contact lens wearers.

14 Claims, No Drawings

USE OF OPHTHALMIC AGENT

This invention is directed to the use of an ophthalmic composition comprising a pharmaceutically active agent, in particular ketotifen as an active agent in connection with contact lens, in particular soft contact lens.

Prior art teaches that patients who use topical ophthalmic medications and wear soft contact lens must remove their lenses before drop instillation to prevent absorption of the medication into the lenses (Christensen et al., CLAO Journal, 1998, 227–231). If said contact lens is not removed and said medicament is administered repeatedly, an accumulation of said absorbed medicament is presumed, which might typically cause ocular irritation, hypersensitivity, keratitis and the like.

It has now surprisingly found, that a composition comprising ketotifen or a pharmaceutically acceptable salt thereof, in particular in a concentration of from 0.01 to 0.05%, is compatible with soft contact lens. Consequently, patients do not have to remove their lens when they are in need of said medication. An object of the present invention is therefore the use of ketotifen or a pharmaceutically acceptable salt thereof in the preparation of an eye medicament to treat allergic conjunctivitis in a patient wearing soft contact lens.

A pharmaceutically acceptable ketotifen salt is preferably ketotifen fumarate. The concentration of a ketotifen salt is preferably 0.005 to 0.05%, more preferred 0.01 to 0.03%, and highly preferred 0.025%.

An addressed composition further comprises a non-ionic tonicity agent and is preferably glycerol. The non-ionic tonicity agent is preferably present in an amount such that the total tonicity of the composition has an osmolarity in the range of 230 to 260 milliosmoles, more preferred to 235 to 255 milliosmoles. If glycerol is used, the concentration of glycerol is preferably in the range of 1.5 to 2.5%. A preservative may be present, in particular for multi-dose units, but it is routinely not present in single dose units. Such single dose units are in particular preferred in the context with the present invention.

If a preservative is present, a preferred preservative is benzalkonium chloride. Typically the amount of the preservative is 0.005 to 0.02%, more preferred 0.01%.

An acid or base may be used in small amounts, such as 0.05 to 0.1%, for adjusting the pH of such solution. Preferred is for example the use of small amounts of sodium hydroxide 1N, e.g. 0.075%. The pH of an addressed composition is adjusted to weak acidity for optimization of stability and tolerability, and said pH of weak acidity is understood to mean preferably a pH of 4.4 to 5.8, more preferably a pH of 5 to 5.5, and most preferably a pH of 5.3.

A preferred composition of this invention comprises ketotifen fumarate, in a concentration of 0.01 to 0.04%, glycerol in a concentration of 2 to 2.5%, optionally benzalkonium chloride in an amount of 0.005 to 0.02%, sodium hydroxide, and water. An even more preferred composition comprises ketotifen fumarate, in a concentration of 0.025%, glycerol in a concentration of 2.125%, optionally benzalkonium chloride in an amount of 0.01%, sodium hydroxide, and water.

The ophthalmic compositions mentioned above are useful as eye drops, in particular as unpreserved single dose units. Said eye drops do have a high therapeutic value because they can be used for the treatment and the temporary prevention of itching of the eye due to allergic conjunctivitis, and they can be used for the treatment and prevention of signs and symptoms of seasonal allergic conjunctivitis. Their therapeutic utility has now been greatly improved by the findings of the present invention, which clearly indicate that ketotifen is not significantly absorbed in soft contact lens and is therefore compatible with soft contact lens.

Soft contact lenses are typically classified both by their water content and the ionic nature of the polymer. Soft contact lenses contain typically of from 1 to 85% water, preferably of from 5 to 60% water and in particular of from 25–55% water. A particular generic class of soft contact lens material is called "filcon". Typical examples of a filcon material are nelfilcon, etafilcon, alfafilcon and vifilcon. Accordingly, within the scope of the present invention, the term soft contact lens is preferably referring to a filcon material, more preferably to nelfilcon, etafilcon, alfafilcon and vifilcon material, and most preferably to a nelfilcon material.

Another object of the present invention is a method to treat allergic conjunctivitis in a patient wearing soft contact lens, which method comprises the direct administration of an aqueous eye drop preparation comprising ketotifen or a pharmaceutically active salt thereof, characterized in that said ketotifen is not significantly absorbed in said soft contact lens.

An ophthalmic composition of the present invention may be manufactured by mixing the ingredients, and packaging the resulting mixture, both as known in the art. Sterilization of the composition and the primary package can be effected e.g. by gamma irradiation, by ethyleneoxide treatment, by electron beam, by autoclaving or by steam sterilization. Typical examples are mentioned infra but are not deemed to restrict the scope of the utility of the present invention.

EXAMPLE 1

Multidose Units

| | |
|---|---|
| Ketotifen fumarate | 0.25 mg (0.025%) |
| Benzalkonium chloride | 0.10 mg (0.010%) |
| Glycerol 100% | 21.25 mg (2.125%) |
| Sodium hydroxide 1N | about 0.75 mg (~0.075%) |
| Water for injection ad | ad 1.0 ml |

EXAMPLE 2

Single Dose Units

| | |
|---|---|
| Ketotifen fumarate | 0.25 mg (0.025%) |
| Glycerol 100% | 21.25 mg (2.125%) |
| Sodium hydroxide 1N | about 0.75 mg (~0.075%) |
| Water for injection ad | ad 1.0 ml |

What is claimed is:

1. A method for the treatment of allergic conjunctivitis comprising
    directly administering to the eye surface of a subject in need of treatment for allergic conjunctivitis an effective amount of an aqueous composition comprising ketotifen or a pharmaceutically active salt thereof, wherein said subject is wearing soft contact lenses.

2. The method of claim 1 wherein said ketotifen salt is ketotifen fumarate.

3. The method of claim 1 wherein said ketotifen or pharmaceutically active salt of ketotifen is present in said aqueous composition at a concentration between 0.005% and 0.05%.

4. The method of claim 3 wherein said concentration is between 0.01% and 0.03%.

5. The method of claim 4 wherein said concentration is 0.025%.

6. The method of claim 1 wherein said aqueous composition comprises a non-ionic tonicity agent.

7. The method of claim 6 wherein said non-ionic tonicity agent is glycerol.

8. The method of claim 1, wherein said aqueous composition comprises a preservative.

9. The method of claim 1, wherein said aqueous composition does not contain a preservative.

10. The method of claim 1, wherein said aqueous composition comprises benzalkonium chloride at a concentration of 0.01%, glycerol at a concentration of 2.125%, and sodium hydroxide at a concentration of about 0.075%.

11. The method of claim 1, wherein said aqueous composition comprises glycerol at a concentration of 2.125%, and sodium hydroxide at a concentration of about 0.075%.

12. The method of claim 1, wherein said allergic conjunctivitis is seasonal allergic conjunctivitis and said composition does not contain a preservative.

13. The method of claim 1, wherein said soft contact lenses comprise nelfilcon.

14. The method of claim 4, wherein said soft contact lenses comprise nelfilcon.

* * * * *